United States Patent [19]
Gordon

[11] Patent Number: 6,102,947
[45] Date of Patent: Aug. 15, 2000

[54] SPLINT WITH FLEXIBLE BODY FOR REPAIR OF TENDONS OR LIGAMENTS AND METHOD

[76] Inventor: Leonard Gordon, 2300 California St., Suite 300, San Francisco, Calif. 94101

[21] Appl. No.: 09/007,021

[22] Filed: Jan. 14, 1998

Related U.S. Application Data

[63] Continuation-in-part of application No. 08/504,587, Jul. 20, 1995, Pat. No. 5,723,008.

[51] Int. Cl.[7] .............................. A61F 2/08; A61B 17/00
[52] U.S. Cl. ...................... 623/13.11; 606/151; 606/228
[58] Field of Search .............................. 606/75, 151, 72, 606/60, 228, 232, 233; 623/13; 433/173; 24/456, 704.1, 706

[56] References Cited

U.S. PATENT DOCUMENTS

| | | | |
|---|---|---|---|
| 5,061,283 | 10/1991 | Silvestrini | 623/13 |
| 5,269,783 | 12/1993 | Sander | 606/72 |
| 5,342,376 | 8/1994 | Ruff | 606/151 |
| 5,500,000 | 3/1996 | Feagin et al. | 606/232 |
| 5,722,982 | 3/1998 | Ferreira et al. | 606/151 |
| 5,723,008 | 3/1998 | Gordon . | |

OTHER PUBLICATIONS

Evans et al., "The Application of Force to the Healing Tendon," *Journal of Hand Therapy*, pp. 266–282 (Oct.–Dec. 1993).

Strickland, "Flexor Tendon Injuries: I. Foundations of Treatment," *Journal of American Academy of Orthopedic Surgeons*, vol. 3(1):44–54 (Jan.–Feb. 1995).

Strickland, "Flexor Tendon Injuries: II. Operative Technique," *Journal of American Academy of Orthopedic Surgeons*, vol. 3(1):55–62 (Jan.–Feb. 1995).

Mitsuhiro Aoki et al., "Tendon Repair Using Flexor Tendon Splints: An Experimental Study," *The Journal of Hand Surgery*, vol. 19A(6):984–990 (Nov. 1994).

*Primary Examiner*—David H. Willse
*Attorney, Agent, or Firm*—Flehr Hohbach Test Albritton & Herbert

[57] ABSTRACT

A surgical repair splint (21,41,61,81,121) for use with a securement device such as a plurality of sutures (31,51,71, 91,131) to hold together opposed ends of a member, such as a tendon or ligament (24,64,84,124), during preparing and healing of the member. The repair splint (21,121) has an elongated splint body, which can be flexible and which can either be pushed or pulled into the opposite ends (22,23, 122,123) of the member to be repaired, or placed along a side of the opposed ends. The repair splint further includes securement structures or oppositely facing shoulders (32,33, 132,133) on relatively rigid pointed splint ends (26,27,126, 127) which are formed to receive and cooperate with a securement device, such as sutures (31,131), so as to secure the opposite tendon or ligament ends to the splint against separation of the opposed faces (28,29,128,129) which are to be knit together during healing. A method of surgical repair of ruptured or severed tendon or ligament ends is also provided.

7 Claims, 4 Drawing Sheets

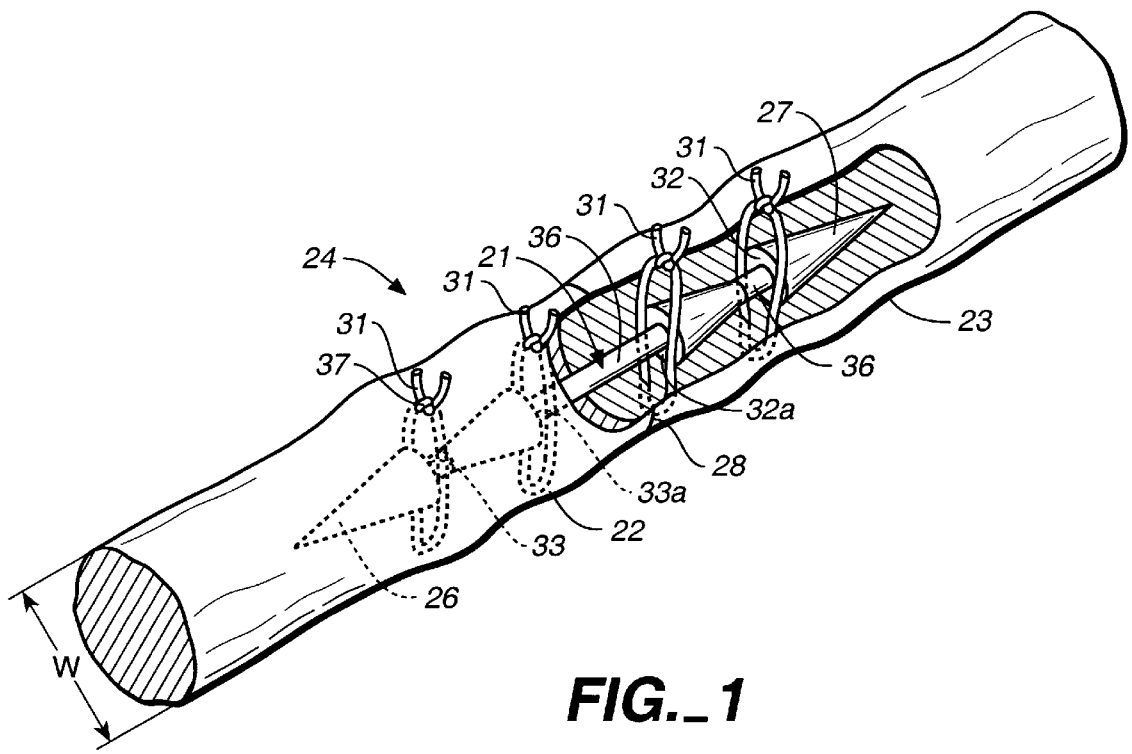
FIG._1
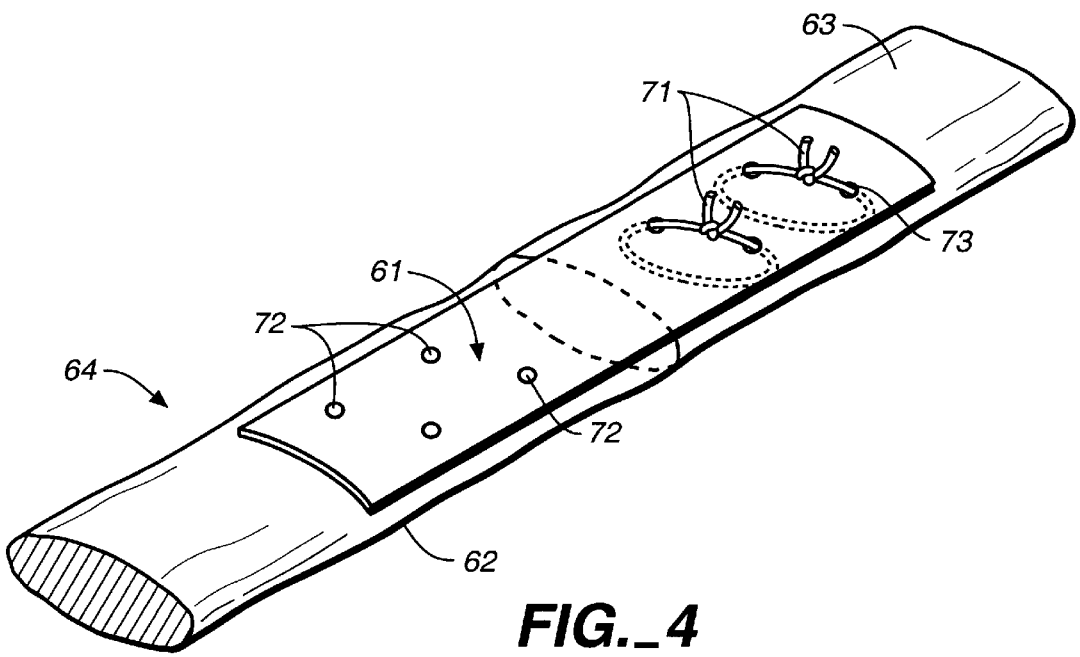
FIG._4

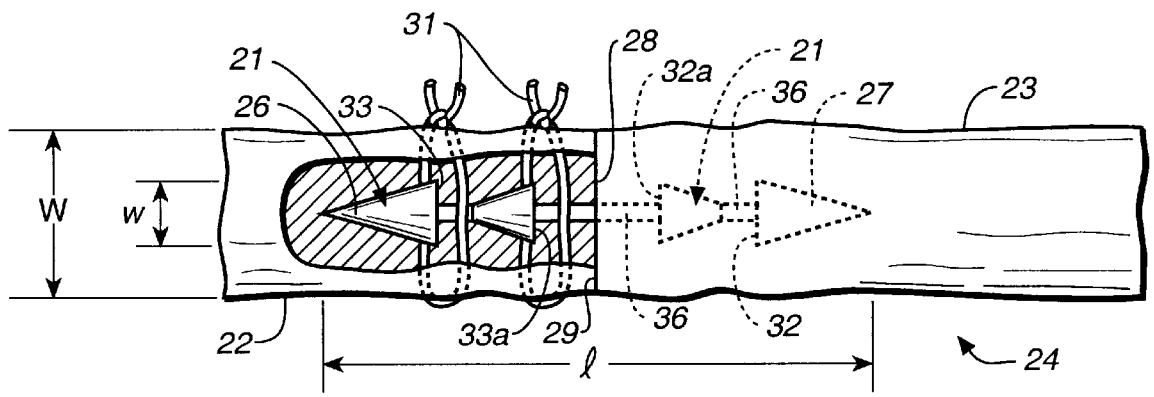
FIG._2
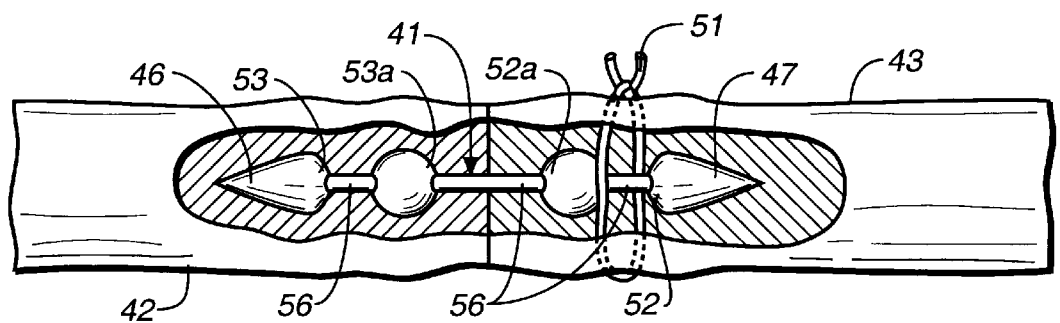
FIG._3

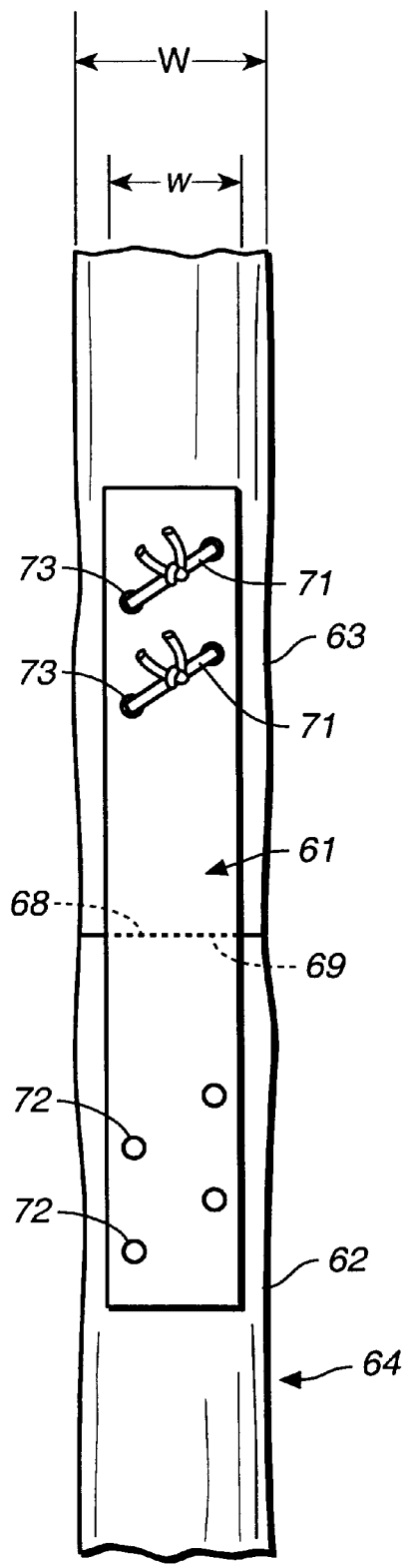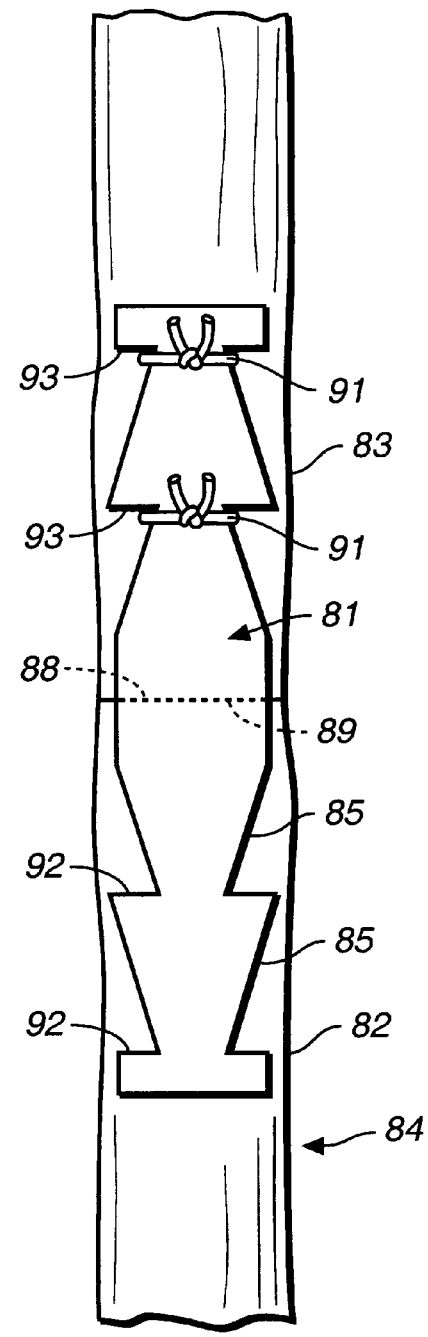
*FIG._5*        *FIG._6*

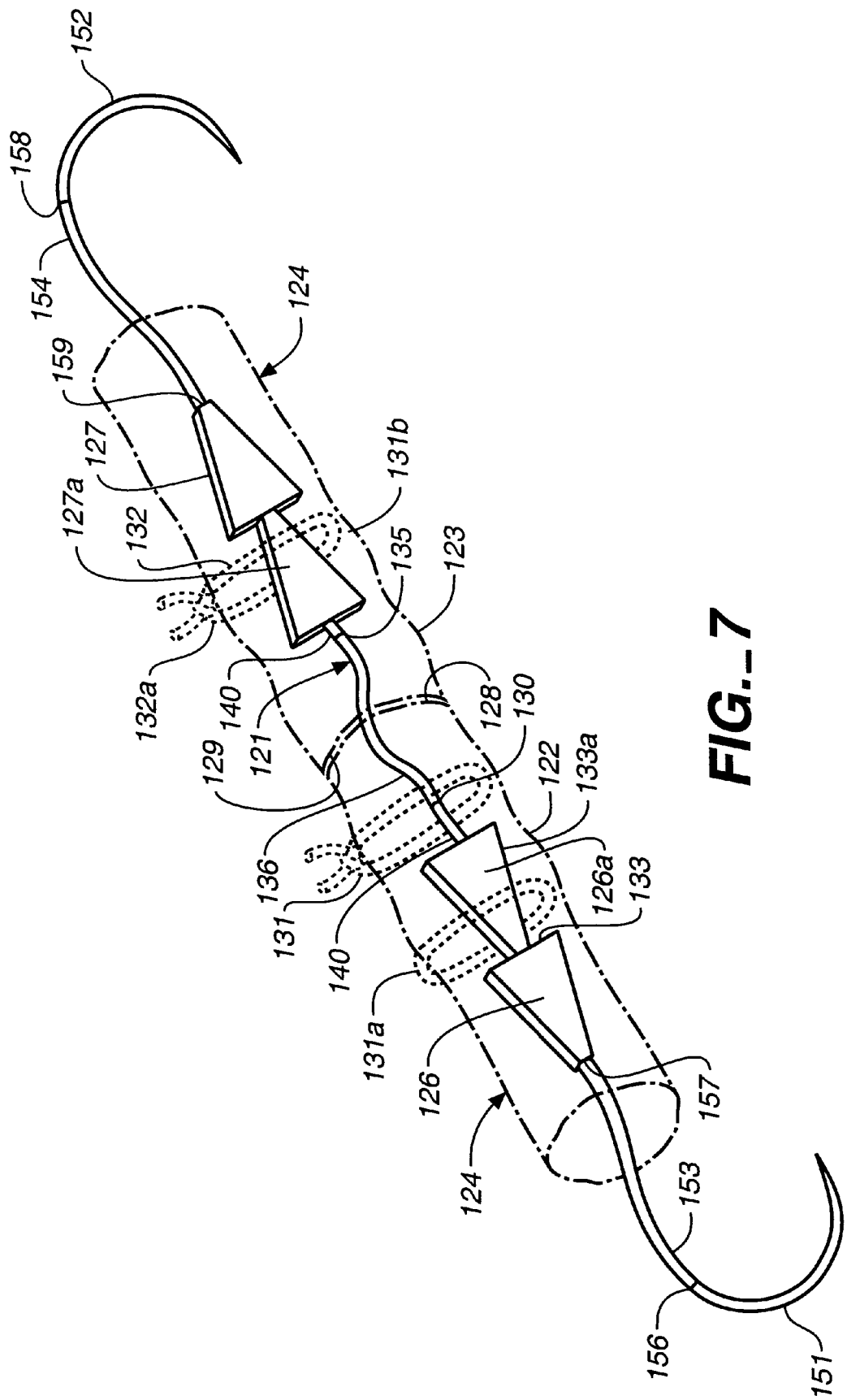
FIG._7

SPLINT WITH FLEXIBLE BODY FOR REPAIR OF TENDONS OR LIGAMENTS AND METHOD

CROSS-REFERENCE TO RELATED APPLICATION

This is a continuation-in-part of my prior application, Ser. No. 08/504,587, filed Jul. 20, 1995, now U.S. Pat. No. 5,723,008.

TECHNICAL FIELD

The present invention relates, in general, to apparatus and methods for repair of ruptured or severed tendons and ligaments, and more particularly, relates to surgical operative techniques for joining together the opposed ends of such members in order to effect repair.

BACKGROUND ART

Surgical repair of tendons and ligaments, and particularly flexor tendons, has been accurately described as a "technique-intensive surgical undertaking." The repair must be of sufficient strength to prevent gapping at the opposed end faces of the repaired member and to permit post-repair application of rehabilitating manipulation of the tendon or ligament.

Considerable effort has been directed toward the development of various suturing techniques to repair severed or ruptured tendons and ligaments. The technique which is probably in most widespread use is by repair of the tendons using various suture techniques. The most common suture technique is known as the Kessler repair, which involves the use of sutures that span in a particular configuration or pattern across the opposed severed ends of the tendon or ligament. There are, however, a wide variety of suturing patterns which have been developed in an effort to attempt to increase the tensile strength across the surgical repair during the healing process. Evans and Thompson in an article entitled "The Application of Force to the Healing Tendon" in the *Journal of Hand Therapy*, October–December, 1993, pages 266–282 survey the various suturing techniques which have been employed in surgical tendon repair, and in two articles by Strickland in the *Journal of American Academy of Orthopaedic Surgeons* entitled "Flexor Tendon Injuries: I. Foundations of Treatment" and "Flexor Tendon Injuries: II. Operative Technique", Volume 3, No. 1, January/February, 1995, pages 44–62, the various techniques also are described and illustrated.

Generally, the tensile force at which a tendon repair joint will fail increases with increased complexity of the suturing scheme. As can be seen from the Evans and Thompson article, the loads which failure occur across a sutured joint can vary between about 1,000 grams to reported failures as high as about 8,000 grams. The Kessler and modified Kessler techniques are relatively simple in their suturing pattern, but they tend to have a failure strength toward the low end of the range, for example, between about 1,500 to 4,000 grams.

As is reported in Evans and Thompson, at least one researcher has employed a Mersilene mesh sleeve having a size slightly larger than the tendon that is sutured to the opposed tendon ends. Using the sleeve experimental failure loading as high as 10,000 grams was reported. Mersilene, which is the material that sutures are often made of, has the disadvantage that human tissue will adhere or experience adhesion to the Mersilene. This is undesirable in flexor tendons and ligaments since the tendon must be able to glide relative to the surrounding tissue during the flexing process. Moreover, a sleeve may be well suited for use with tendons and ligaments which are substantially cylindrical, but it becomes less easily employed with tendons having a flat or ovaloid cross section.

In an article by Mitsuhiro, et al. in *The Journal of Hand Surgery*, Vol. 19A, No. 6, November, 1994, pp 984–990, entitled "Tendon Repair Using Flexor Tendon Splints: An Experimental Study" techniques are described for surgically repairing tendons using a tendon splint. In one approach the opposed tendon ends are slit and the splint, a generally rectangular Dacron member, spans across and is positioned in each slit tendon end. This internally positioned splint is then sutured in place across the tendon ends using various suturing patterns. In another approach described in the Mitsuhiro, et al. article, the rectangular splint is sutured to the back side of the tendons across the severed ends. As noted by Mitsuhiro, et al., both these techniques have disadvantages. The positioning of a splint internally by slitting the tendon ends may damage tendon blood supply, and the external positioning of a Dacron splint can interfere with tendon gliding.

Accordingly, development of surgical tendon and ligament repair techniques that are less technique-intensive and yet have a high strength across the repaired joint is a highly desirable goal. Such repair techniques should minimize the adhesion potential and permit member excursions during manipulation to effect rehabilitation.

It is an object of the present invention, therefore, to provide a tendon or ligament splint which can be used to splint together opposed ends of the tendon or ligament in a relatively simple procedure to provide enhanced joint strength.

A further object of the present invention is to provide a tendon or ligament splint and method which have improved compatibility with the body and are suitable for joining flexor tendons and ligaments, which normally must experience substantial longitudinal excursions without adhesion to surrounding tissue.

Still another object of the present invention is to provide a surgical method of repairing or joining together opposed tendon or ligament ends which is less tedious and time-consuming and yet provides a high-strength, body-compatible tendon joint.

The surgical tendon or ligament splint and method of the present invention have other objects and features of advantage which will become apparent from, and are set forth in more detail in, the accompanying drawing and following description of the Best Mode of Carrying Out The Invention.

DISCLOSURE OF INVENTION

A surgical repair splint is provided for use with a securement device, such as one or more sutures, to repair or hold together opposed end faces of a ruptured or severed tendon or ligament during the healing or knitting of the ends together. In one embodiment the elongated splint is provided with a relatively flexible central splint body, for example, a metallic suture, to which a pair of relatively rigid pointed splint ends are coupled. The splint ends can be oppositely facing frusto-conical members which have pointed ends that penetrate the opposed ends of the tendon or ligament and provide wide ends that act as shoulders across which transverse sutures can extend to resist separation of the tendon or ligament ends. A needle and tendon can be secured to each pointed splint end to enable the splint to be pulled into the tendon or ligament ends for securement to the tendon by a transverse suture.

In another embodiment the splint takes the form of a thin, flat metal strip having a length dimension sufficient to extend inwardly of each of the opposed ends by a distance enabling securement of the splint body to each of the opposed ends of the member by the securement device, e.g., a transversely extending suture. Additionally, the splint body further is formed with a securement structure, such as a shoulder or hole, proximate each opposed splint end having a configuration which cooperates with the securement device to resist axial displacement of the end faces away from each other. In both embodiments the splint is formed with a width dimension less than the width dimension of the opposed tendon or ligament end faces so that it will not significantly impede longitudinal excursions of the tendon or ligament during healing.

In a further aspect of the present invention, a method of joining together opposed ends of a ruptured or severed tendon or ligament is provided which is comprised, briefly, of the steps of positioning the opposed ends in axially aligned and substantially abutting relationship, placing an elongated splint having securement structures thereon in a position to span across the opposed tendon or ligament ends, adhering each of the opposed ends to the securement structures provided on the splint, preferably by suturing, and allowing the opposed ends to knit together while sutured to the splint. In one embodiment, the placing step is accomplished by penetrating the opposed end faces of the tendon or ligament with an elongated splint having pointed splint ends and a width dimension less than the opposed ends of the tendon or ligament into the opposed end faces of the tendon or ligament until the opposed tendon ends are axially aligned and in substantially abutting relationship to permit securement, preferably by suturing, of the opposed ends to the splint.

BRIEF DESCRIPTION OF THE DRAWING

FIG. 1 is a top perspective, schematic view of a tendon or ligament having a surgical repair splint constructed in accordance with the present invention embedded therein and sutured thereto.

FIG. 2 is a side elevation view, partially broken away, of the tendon or ligament repair of FIG. 1.

FIG. 3 is a side elevation view corresponding to FIG. 2 of an alternative embodiment of the microsurgical repair splint of FIGS. 1 and 2.

FIG. 4 is a top perspective, schematic view of a flat tendon or ligament showing a further alternative embodiment of the microsurgical repair splint of the present invention sutured to a side thereof.

FIG. 5 is a top plan view of the assembly shown in FIG. 4.

FIG. 6 is a top plan view of an alternative embodiment of the splint of FIGS. 4 and 5.

FIG. 7 is a side elevation view of a further alternative embodiment of the splint of the present invention showing placement needles and showing, in phantom, a tendon and securement sutures.

BEST MODE OF CARRYING OUT THE INVENTION

The present invention provides an elongated splint for use in surgical repairs of tendons, ligaments and similar elongated tissue that can become severed or ruptured or otherwise separated. The object of any such repair is to join the opposed ends of the severed member at a repaired joint which has sufficient strength that it will be effective in holding the ends together during healing. In connection with tendons and ligaments, and particularly flexor tendons, it is generally thought to be highly desirable to be able to manipulate or apply passive or active stress to cause longitudinal excursions of the tendon under low loading to encourage rehabilitation.

While such repairs can be effected, as indicated above, through the use of sutures alone, in the apparatus and method of the present invention tendon joining repair splints are provided which can be relatively easily used to produce substantially enhanced tendon and ligament repairs. While most preferably applied to humans, it also will be appreciated that the apparatus and method of the present invention are suitable for use for repairs in other animals.

Referring now to FIGS. 1 and 2, an elongated surgical repair splint member, generally designated 21, is shown embedded in the opposed ends 22 and 23 of a ligament, tendon or other elongated tissue member 24 of the type which experiences longitudinal excursions during use. Tendon or ligament 24 has been severed or ruptured and accordingly has opposed tendon ends 22 and 23, which can be seen to be substantially axially aligned. End faces 28 and 29 of the tendon or ligament are in substantially abutting relationship, and in the form of repair splint shown in FIGS. 1 and 2, entire splint 21 is embedded inside ends 22 and 23 of member 24. Accordingly, in the embodiment of the present invention of FIGS. 1 and 2, splint 21 has a width dimension, w, which is less than the nominal width dimension, W, of member 24 and member ends 22 and 23. As will be appreciated, the representation in the drawings is schematic and the tendon ends will not be perfectly cylindrical, nor will their width dimensions be constant.

The length dimension, 1, of splint 21 between the opposite ends 26 and 27 of the splint body will be sufficient to extend inwardly of each of the opposed end faces 28 and 29 of tendon ends 22 and 23 by a distance enabling securement of splint 21 to each of ends 22 and 23 by at least one securement device, which is preferably provided by at least one transversely extending suture, such as sutures 31.

In order to enable embedding of splint 21 into tendon or ligament ends 22 or 23, it is preferable that opposite splint ends 26 and 27 are formed to enable easy urging or penetration into the tendon ends, for example, by providing a tapered or pointed end. In the illustrated form of the splint of FIGS. 1 and 2, the splint body is formed with oppositely facing conical splint ends 26 and 27 which can be driven, or urged by pulling as described in connection with the embodiment of FIG. 7, into tendon end faces 28 and 29 and urged axially along tendon ends 22 and 23 until tendon faces 28 and 29 are in substantially abutting relation and the splint is positioned substantially as shown in FIGS. 1 and 2. This structure avoids tedious tendon end slitting, as described in the Mitsuhiro, et al. article, and minimizes the trauma to the tendon ends.

Moreover, tendon or ligament repair splint 21 of the present invention further includes a securement structure 32, 33, formed to cooperate with a securement device, such as a suture, resist relative axial displacement between splint body 21 and device or sutures 31. In the form of the splint of FIGS. 1 and 2, the splint securement structures are provided by oppositely facing ridges or shoulders 32 and 33 against which sutures 31, or tendon tissue pulled inwardly by the suture, will bear if an axial force is applied to tendon or ligament 24 in a direction tending to separate faces 28 and 29. In the illustrated splint 21, a second set of suture securement shoulders 32a and 33a are provided by a second frusto-conical portion of the splint body. This allows two sutures 31 to extend transversely across each of tendon ends 22 so as to pick up the oppositely facing suture securement shoulders 32, 32a and 33, 33a. In FIG. 2, the sutures in end 23 have been omitted for clarity of illustration.

In order to secure the sutures 31 to splint securement structure 32, 32a and 33, 33a, the suture is first sewn into a tendon or ligament end at a position immediately proximate the small diameter or neck portion 36 immediately adjacent a selected one of the suture securement shoulders. The surgeon then comes back through the tendon end from the other side closely proximate an opposite side of neck portion 36 and exits near the original entry into the tendon end. The suture can then be cinched down and tied off so that the loop formed in the tendon around the repair splint neck portion 36 traps the splint as embedded in the tendon or ligament end. Thus, only the tied off suture ends extend outside the tendon or ligament, and they present little resistance to longitudinal excursion of the tendon during healing. The embedded splint assembly also has little tendency to adhere to surrounding tissue, again permitting longitudinal excursions.

As will be understood, therefore, the procedure for placement of the splint of the present invention and securement of the same to the tendon or ligament ends is relatively simple. The suturing requires considerably less manipulation of the tendon or ligament than some of the complex suturing patterns or schemes employed in the prior art. Moreover, as will be set forth below, the resulting repaired joint has a strength which is at least equal to the best and most complex suturing patterns, and is greatly enhanced over the relatively simple and most often used suturing techniques.

While use of the microsurgical repair splint of the present invention has been illustrated with a plurality of discrete sutures 31, it will be understood that other suture techniques, such as a single, running suture, also could be used with any splint of the present invention to secure the splint to the tendon or ligament ends.

It will be understood, however, that securement devices other than sutures could be employed with the present split. Thus a surrounding elastic member or band could cooperate with securement shoulders 32, 32a and 33, 33a. Similarly, a band or strip with hook-and-loop fasteners (e.g., VELCRO) could be employed.

FIG. 3 illustrates an alternative embodiment of the surgical tendon and ligament repair splint shown in FIGS. 1 and 2. In FIG. 3 a splint 41 is provided which again has pointed splint ends 46 and 47 to enable the same to be easily embedded in opposed tendon or ligament ends 42 and 43. Instead of securement shoulders which are perpendicular, splint 41 includes curved or spherical enlargements 52, 52a and 53, 53a, which are spaced axially along neck portion 56 of the splint body. Sutures, or another securement device, 51 again will be placed sufficiently close to the rounded suture securement shoulders 52, 52a and 53, 53a that, when cinched down around neck portions 56, axial separation of tendon or ligament ends 42 and 43 will require substantial force.

In an embodiment not shown in the drawing, the splint body of the present invention can be formed with a securement structure taking the form of an aperture in the body. Thus, for the embedded form of the invention, the splint would have oppositely facing pointed ends, but in a wide portion of the splint body a transversely extending aperture would be provided in each end dimensioned so that the surgeon could suture through the aperture when the splint was embedded in the tendon body. This requires some additional technique, but because the aperture would be located in a known relationship to the wide portion of the splint body, the surgeon can palpate the tendon or ligament end to locate the wide portion is and thereby determine the location of the aperture. Moreover, in order to angularly orient the aperture about a longitudinal axis, the splint body could be flat but formed with sharp ends which avoid the necessity of slitting the tendons, as described in Mitsuhiro, et al. The orientation of the aperture could be determined by palpation.

Referring now to FIGS. 4 and 5, a further alternative embodiment of the tendon or ligament surgical repair splint of the present invention is shown. The embodiment shown in FIGS. 4 and 5 is particularly well suited for use on tendons or ligaments which are relatively flat or ovaloid in their cross section. Such flat tendons may be found, for example, as extensor tendons in the human hand. Embedding a repair splint in a flat tendon or ligament may be difficult or impossible. It is also possible, however, as above described, to form an embedded splint as a flat member, rather than a member which is a surface of revolution about the longitudinal axis of the member to be joined.

The splint, generally designated 61, of FIGS. 4 and 5 can be formed with an elongated body in the form of a thin, flat metal strip having a width dimension, w, not substantially greater than the width dimension, W, of tendon ends 62 and 63 and a length dimension sufficient to span across the opposed end faces 68 and 69 of the tendon or ligament ends 62 and 63 by a distance enabling suturing to each end. In the flat strip-like form of the splint of the present invention, securement structures advantageously may be formed as a plurality of apertures 72 and 73 dimensioned so that sutures 71 can be sewn therethrough. When the sutures 71 are cinched down and tied off, they will pull the thin splint 61 into general conformance with the outside surface of tendon or ligament ends 62 and 63. Thus, the thin cross section of splint 61 allows it to conform closely to the exterior configuration of the tendon or ligament ends, and the metal body provides significant tensile strength across the severed or ruptured end faces 68 and 69. As used herein, the expression "thin" shall mean strip stock having a thickness dimension not greater than about 0.2 millimeters, and preferably less than 0.1 millimeter. The preferred splint material for the splint 67 of FIGS. 4 and 5 is medical grade stainless steel since it is corrosion resistant and has high strength in very thin sections, but other metal alloys having high corrosion resistance can be used. Stainless steel and other metal alloys also will be smooth and in thin sections will conform to the member being repaired and glide smoothly along surrounding tissues during longitudinal excursions of the tendon. Such smooth stainless steel splints also will tend not to adhere to surrounding tissues.

As will be appreciated, it also would be possible to employ a pair of strip-like splints 61 on each side of relatively flat tendon or ligament 64 so as to provide further strength across the joint between the member ends. It has been found that for many applications, however, that only a single splint 61 needs to be employed to achieve ultimate tensile strength across the joint which is at least twice that of a standard Kessler suture technique. Nevertheless, further strength would be achieved through the use of a second repair splint, although there would be attendant time required to secure the same to the tendon or ligament ends.

In FIG. 6, a further alternative embodiment of strip-type repair splint of the present invention is shown. Repair splint 81 again is formed from a thin, flat metal strip having a length sufficient to span across the opposed faces 88 and 89 of tendon or ligament ends 82 and 83. The width dimension is again preferably not substantially greater than the nominal width dimension of the ends 82 and 83 of the member to be joined together so as not to protrude laterally of the member. Since thin strips will conform to the tendon when cinched down excess width can be tolerated by pulling the strip down around the tendon or ligament. In the extreme the strip can wrap completely around the tendon.

In the embodiment shown in FIG. 6, the securement structure is provided by notches 85 in oppositely facing sides of strip 81 that afford oppositely facing shoulders or ridges 92 and 93 against which a securement device, such as sutures 91, can bear. Again, repair splint 81 is sutured to a side of member 84 which is to be repaired, and splint 81 can advantageously be formed from a medical grade stainless steel material. Alternatively, the side of splint 81 contacting the tendon or ligament can be formed as a roughened surface which will adhere to the tendon or ligament ends when secured in place by a securement device, which could include an adhesive.

Referring now to FIG. 7, an alternative embodiment of the present splint is shown which is similar to the embodiment of FIGS. 1 and 2.

Surgical repair splint 121 is shown embedded in a tendon or ligament member (phantom) 124 which has been ruptured or severed and has aligned, opposed ends 122 and 123 with abutting end faces 128 and 129. In the embodiment of FIG. 7, splint 121 has a central splint body 136 which is flexible relative to the pair of opposite facing splint ends 126, 126*a* and 127, 127*a* to which central body 136 is coupled.

In the preferred form, central splint body 136 is provided by a medical grade stainless suture, for example, No. 5 to No. 10 (diameter) stainless suture material. Opposite ends of central splint body can be swaged at 130 and 135 to splint ends 126 and 127 by stems 140 provided on the innermost splint ends 126*a* and 127*a* using a swaging technique well known in the medical industry in connection with securing sutures to needles.

The splint ends 126, 126*a* and 127, 127*a* can be formed of cast, machined or otherwise formed metal or plastic material which is both pointed and sufficiently rigid to enable penetration of end faces 128 and 129 of the tendon or ligament 124. When central splint portion 136 is a flexible stainless steel suture, splint ends 126, 126*a* and 127, 127*a* are preferably also formed of medical grade stainless steel. If flexible splint central body 136 is formed from a flexible plastic or synthetic material, ends 126, 126*a* and 127, 127*a* advantageously may be similarly formed, either monolithically with central splint body 136 or adhesively secured to central splint body 136.

Splint ends 126, 126*a* and 127, 127*a* are shown as being provided by two triangular members with pointed ends facing away from each other and large diameter ends facing toward central splint body 136 and each other. A single triangular member also could be used, and it also will be understood that splint ends also could be frusto-conical members as shown in FIGS. 1 and 2. The thickness dimension of triangular splint ends 126, 126*a* and 127, 127*a* preferably is about equal to the diameter of central splint body 136.

The large diameter ends 133, 133*a* of splint end 126, 126*a* and the large diameter ends 132, 132*a* of splint end 127, 127*a* provide oppositely facing shoulders which act as securement structures against which a securement device, such as a transverse suture 131 may cooperate to secure the tendon ends 122 and 123 against axial separation.

Three types of securement devices are shown in phantom in FIG. 7, namely, a resilient band 131*a* around an exterior of tendon or ligament 124. Band 131*a* pulls the tendon tissue behind shoulder 133 radially inwardly to resist displacement of tendon end 122 to the left in FIG. 7. Securement device 131 is a single suture sewn through the tendon end proximate and inwardly or behind shoulder 133*a*. Finally, securement device 131*b* is a single running suture sewn across tendon end 123 behind or inwardly of both shoulders 132 and 132*a*.

As thus far described, splint 121 could be embedded into tendon or ligament 124 using a pushing instrument (not shown). Thus, the pointed ends 126 and 127 could be urged or driven by an instrument into each of end faces 128 and 129 of tendon or ligament 124. In the preferred form illustrated in FIG. 7, however, splint 121 has at least one needle, and preferably a pair of needles 151 and 152, secured to splint ends 126, 126*a* and 127, 127*a*. Needles 151 and 152 are coupled to pointed splint ends 126 and 127 by flexible sutures or threads 153 and 154, which again can be either 4.0 to zero (diameter) stainless steel or braided polyester (TYCRON)material of the type which is conventionally used in needle/suture assemblies. Thus, needle 151 will be joined at 156 to flexible suture 153, which in turn is joined at 157 to pointed end 126 of the splint end 126, 126*a*. Needle 152 will be joined at 158 to flexible suture 154 which is coupled at 159 to pointed end 127 of splint end 127, 127*a*.

In use, one of the needles 151 and 152 is urged into one of end faces 128 and 129, and the needle is advanced axially up the corresponding tendon end 122 or 123 until it is well beyond the farthest position at which the splint end 126 or 127 is to reach. The needle is then advanced through a side wall of the tendon or ligament end and used to pull the corresponding splint end, either 126 or 127, axially into the tendon until the end reaches the position shown in FIG. 7. The process is repeated for the other needle and the other tendon end.

The two sutures 153 and 154 attached to the splint ends are pulled axially in opposite directions until end faces 128 and 129 are in abutting relation and flexible splint body 136 is tensioned. Flexible sutures 153 and 154 may be cut off flush with the side wall of the tendon to remove needles 151 and 152. Transverse securement devices 131, 131*a* or 131*b* are preferably used to secure tendon ends 122 and 123 to shoulders 132, 132*a* and 133, 133*a* of the splint to resist separation of the tendon ends before cutting off needles 151 and 152.

Having described the surgical splint apparatus of the present invention, the method of joining together opposed ends of a ruptured or severed tendon or ligament can be set forth. The method of the present invention includes the steps of positioning opposed ends of the member to be joined together in substantially axially aligned and substantially abutting relationship. Most preferably, the end faces of the tendon ends are abutting to form a butt joint, but other joints such as lap joints can be formed using the repair splint and method of the present invention.

In one aspect of the method of the present invention, the first step is urging an elongated repair splint having a width dimension less than the opposed ends into each end of the tendon or ligament, either by pushing the splint into the tendon end face or pulling into the end face, as described in connection with FIG. 7. The repair splint is urged into the tendon ends until the opposed faces of the member ends are substantially abutting so that they will be held together for knitting and biological reconstruction. Finally, the method includes the step of securing each of the opposed tendon or ligament ends to a securement structure on the splint to secure the opposed ends to the splint while embedded therein.

Thereafter, the present method can include the steps of allowing the opposed ends to knit together while sutured to the splint.

In another aspect of the method of the present invention, the repair splint is applied to the severed or ruptured tendon or ligament by the step of placing an elongated, thin, flat metallic strip splint in a position to span across opposed faces of the member ends by a distance which is sufficient to enable suturing of opposite splint ends to the opposed tendon or ligament ends. The splint is placed in contact with a side of the member to be joined and preferably has a width dimension not substantially greater than the width dimension of the member to be joined. The repair splint is formed with securement structure proximate each of the splint ends, and, as above described, the next step is to secure each of the opposite splint ends of the flat splint to the member ends to be joined while they are in aligned and abutting relationship.

The following Table 1 illustrates the improvement in strength possible by using the surgical repair splints of the present invention, as compared to an intact tendon and a standard Kessler repair technique. All measurements were made on an Instron tensiometer.

The metal splints were constructed as shown in FIGS. 4 and 5 with a width dimension, w, of 4 millimeters, a length dimension, 1, of 30 millimeters and a thickness dimension of 0.5 millimeters from stainless steel. A staggered suture securement aperture pattern, as shown in FIG. 5, was employed. The embedded splint with cones was constructed as shown in FIGS. 1 and 2 and had an overall length dimension of 18 millimeters with a maximum width dimension of three millimeters. The distance between the first pair of opposed shoulders 32a and 33a was six millimeters and the distance from shoulders 32a to end 27 and 33a to end 26 was also six millimeters. The diameter of neck portion 36 was one millimeter, and the splint was made from stainless steel. Other materials could be used.

As will be seen from Table 1, the embedded surgical repair splint of the present invention had an ultimate joint strength of more than four times that of a standard Kessler repair. The flat metal repair splints had an ultimate repair strength across the joint of two-to-three times that of a Kessler repair.

The surgical repair splints of the present invention also can be formed of a material which is capable of being absorbed by the body over time so that the splint does not have to be removed. Thus, a polylactate material or a material made from polyglycolic acid are examples of absorbable materials having sufficient tensile strength to provide high strength to the repaired joint. Other absorbable materials would be suitable provided that they have sufficient tensile strength. In connection with the flat strip-like repair splints, it is also possible to come back in and remove the splint, particularly if it is a metal splint, so that prolonged contact with the body will not cause corrosion or infection. Obviously, it is preferable that if an embedded repair splint is made of a metal, which is possible, that it is made of a surgical grade stainless steel or other metal alloy capable of being embedded substantially indefinitely in a patient. Similarly, such metal alloy splints can be employed with a strip splint and the splint left in place.

What is claimed is:

1. A surgical repair splint for holding together opposed member ends of a severed or ruptured tendon or ligament during healing of said member comprising:

a relatively flexible length of suture material providing central splint body having opposed body ends;

a pair of pointed splint ends formed of a relatively rigid material for penetration of said opposed member ends and coupled to said opposed body ends with said pointed splint ends facing away from each other, said pointed splint ends further each having a transverse shoulder facing toward said central splint body dimensioned for receipt of a transversely extending suture proximate said shoulder to resist axial separation of said opposed member ends during excursion of said member;

flexible sutures attached at one end to each of said pair of pointed ends;

needles attached to an opposite end of each flexible suture; and

TABLE 1

Strengths of an intact tendon and of various cut tendon's repairs.

| PARAMETERS | MAX. LIN. TENSILE STRENGTH (lb) | SIGMA (lb/mm$^2$) | EPSILON (mm/mm) elongation | STIFFNESS | RESILIENCE | ULTIMATE TENSILE STRENGTH (lb) |
|---|---|---|---|---|---|---|
| Types of Repair | | | | | | |
| 1. Intact tendon | 57.34 ± 10.55 | 9.23 ± 2.31 | 0.65 ± 0.22 | 15.22 ± 4.49 | 3.18 ± 1.78 | 62.24 ± 9.03 |
| 2. Standard Kessler | 4.44 ± 0.56 | 0.44 ± 0.04 | 1.78 ± 0.22 | 0.25 ± 0.05 | 0.39 ± 0.02 | 4.72 ± 0.28 |
| 3. Embedded with cones | 16.57 ± 0.34 | 1.09 ± 0.02 | 0.85 ± 0.15 | 1.33 ± 0.24 | 0.47 ± 0.09 | 19.00 ± 1.67 |
| 4. Metal strip splint (a) | 11.52 ± 2.33 | 0.77 ± 0.14 | 1.59 ± 0.20 | 0.50 ± 0.13 | 0.60 ± 0.08 | 13.28 ± 1.22 |
| 5. Metal splint (b)[(2)] | 9.05 ± 0.35 | 0.59 ± 0.04 | 1.20 ± 0.00 | 0.49 ± 0.03 | 0.35 ± 0.02 | 10.70 ± 0.10 | said central splint body, said splint ends, said sutures and said needles each having a width dimension less than a nominal width dimension of said member.

2. The surgical splint as defined in claim 1 wherein, said central splint body is provided by a metal suture material and said pointed splint ends are provided by triangular metallic ends.

3. The surgical splint as defined in claim 2 wherein, said suture material and said pointed splint ends are all made from medical grade stainless steel.

4. A surgical repair splint in combination with a securement device to hold together opposed member ends of a severed or ruptured flexor tendon or ligament member subject to axial excursions during healing of said member comprising:

an elongated flexible central splint body;

pointed relatively rigid opposite splint ends coupled to said central splint body and formed to penetrate into each of said opposed member ends, said splint having a length extending inwardly of each of said opposed member ends by a distance sufficient to enable securement of said splint ends to said member on opposite sides of said opposed member ends, and said splint ends further being formed with a shoulder facing toward said central splint body;

said central splint body and said splint ends having a width dimension less than a nominal width dimension of said member; and a securement device formed to engage said member without protruding from said member by an amount sufficient to impede excursions of said member, said securement device being positioned between the shoulders and formed to cooperate with the shoulders to resist axial separation of said opposed ends during excursions of said member during healing.

5. The splint and securement device as defined in claim 4 wherein, said securement device is provided by at least one suture extending around a portion of said splint body between each said shoulder.

6. The splint and securement device as defined in claim 4 wherein, said central splint body is provided by a length of suture material;

said pointed relatively rigid splint ends are provided by triangular members and said shoulders are provided by large ends of said triangular members.

7. The splint and securement device as defined in claim 4, and a length of flexible suture material secured to each of said splint ends and adapted to extend transversely through a side wall of said member.

* * * * *